(12) United States Patent
Fukui et al.

(10) Patent No.: US 10,041,888 B2
(45) Date of Patent: Aug. 7, 2018

(54) SURFACE DEFECT INSPECTING DEVICE AND METHOD FOR HOT-DIP COATED STEEL SHEETS

(71) Applicant: NISSHIN STEEL CO., LTD., Tokyo (JP)

(72) Inventors: Keita Fukui, Tokyo (JP); Syunsuke Shiga, Tokyo (JP)

(73) Assignee: NISSHIN STEEL CO., LTD., Tokyo (JP)

( * ) Notice: Subject to any disclaimer, the term of this patent is extended or adjusted under 35 U.S.C. 154(b) by 0 days.

(21) Appl. No.: 15/717,703

(22) Filed: Sep. 27, 2017

(65) Prior Publication Data

US 2018/0017503 A1   Jan. 18, 2018

Related U.S. Application Data

(63) Continuation of application No. PCT/JP2016/059963, filed on Mar. 28, 2016.

(30) Foreign Application Priority Data

Mar. 31, 2015 (JP) ................................. 2015-070692

(51) Int. Cl.
*G01N 21/84* (2006.01)
*G01N 21/892* (2006.01)
(Continued)

(52) U.S. Cl.
CPC ....... *G01N 21/892* (2013.01); *G01N 21/4738* (2013.01); *G01N 21/55* (2013.01); *G01N 33/20* (2013.01); *G01N 2201/12* (2013.01)

(58) Field of Classification Search
CPC ............... G01N 25/72; G01N 2021/88; G01N 2021/556; G01N 2021/8918;
(Continued)

(56) References Cited

U.S. PATENT DOCUMENTS

| 4,759,072 A | * | 7/1988 | Yamane | G01N 21/89 250/330 |
| 5,087,822 A | * | 2/1992 | Fairlie | G01N 21/8903 250/559.16 |
| 6,630,996 B2 | * | 10/2003 | Rao | G01N 21/9501 356/237.1 |

(Continued)

FOREIGN PATENT DOCUMENTS

| JP | 4-315952 A | 11/1992 |
| JP | 8-82604 A | 3/1996 |

(Continued)

OTHER PUBLICATIONS

International Search Report for PCT/JP2016/059963, dated May 24, 2016, Total of 4 pages.

*Primary Examiner* — Hoa Pham
(74) *Attorney, Agent, or Firm* — Lynette Wylie; Apex Juris, pllc.

(57) ABSTRACT

A surface defect inspecting device for hot-dip coated steel sheets comprising: an illuminating unit for illuminating an imaging target portion on a hot-dip coated steel sheet; a specular reflection light imaging unit for imaging specular reflection light from the imaging target portion; a diffuse reflection light imaging unit for imaging diffuse reflection light from the imaging target portion; and an image signal processing unit for processing specular reflection image and diffuse reflection image signals, the specular and diffuse reflection light imaging units simultaneously imaging light reflected from the imaging target region, the image signal processing unit extracting a portion having brightness level lower than a predetermined threshold, as a defect portion, from the specular reflection image signal, and threshold processing the diffuse reflection image signal, with respect to a portion corresponding to an extracted defect portion, to determine a defect type by classifying the extracted defect portion.

4 Claims, 7 Drawing Sheets

(51) Int. Cl.
*G01N 21/47* (2006.01)
*G01N 33/20* (2006.01)
*G01N 21/55* (2014.01)

(58) Field of Classification Search
CPC ........... G01N 2021/8887; G01N 21/55; G01N 21/47; G01N 33/20
USPC .......................................... 356/237.1–237.5
See application file for complete search history.

(56) References Cited

U.S. PATENT DOCUMENTS

| | | | | |
|---|---|---|---|---|
| 7,248,366 B2* | 7/2007 | Uesugi | ................. | B21O 51/005 356/237.2 |
| 7,286,234 B2* | 10/2007 | Zhou | ..................... | G01N 21/00 356/237.1 |
| 7,423,744 B2* | 9/2008 | Uesugi | ................... | G01N 21/89 356/237.2 |
| 7,599,052 B2* | 10/2009 | Uesugi | ................... | G01N 21/89 356/237.2 |

FOREIGN PATENT DOCUMENTS

| | | | |
|---|---|---|---|
| JP | 8-278258 | A | 10/1996 |
| JP | 11-183396 | A | 7/1999 |
| JP | 11-183397 | A | 7/1999 |
| JP | 2004-151006 | A | 5/2004 |
| JP | 2006-177746 | A | 7/2006 |
| JP | 2010-249685 | A | 11/2010 |
| JP | 2012-103017 | A | 5/2012 |
| JP | 5594071 | B | 9/2014 |
| JP | WO2016/158873 | A1 | 10/2016 |

\* cited by examiner

| No | Brightness level of reflection image signals | | | | Aspect ratio | Roundness | Direction | Defect type |
|---|---|---|---|---|---|---|---|---|
| | Specular reflection image signals | | Diffuse reflection image signals | | | | | |
| | Dark/Bright | Density | Dark/Bright | Density | | | | |
| 1 | Dark | a1 < A | Dark | b1 < B | | | | Non-coating |
| 2 | Dark | A < a2 | Dark | B < b2 | | | | Pin-hole non-coating |
| 3 | Dark | a3 < A < a3' | Dark | b3 < B < b3' | c3 < C | | e3 < E < e3' | Scab |
| 4 | Dark | a4 < A | Bright | b4 < B | | | | Dross |
| 5 | Dark | a5 < A | Bright | b5 < B | C < c5 | | | Dirt 1 |
| 6 | Dark | a6 < A | Bright | b6 < B | c6 < C | D < d6 | | Dirt 2 |

SURFACE DEFECT INSPECTING DEVICE AND METHOD FOR HOT-DIP COATED STEEL SHEETS

CROSS REFERENCE TO RELATED APPLICATIONS

This is a continuation application of International Patent Application No. PCT/JP2016/059963 filed on Mar. 28, 2016 claiming priority upon Japanese Patent Application No. 2015-070692 filed on Mar. 31, 2015, of which full contents are incorporated herein by reference.

BACKGROUND OF THE INVENTION

Field of the Invention

The present invention relates to a surface defect inspecting device and method for hot-dip coated steel sheets.

Description of the Background Art

There has been a variety of surface defects, such as non-coating, scab, dross, dirt, generated on hot-dip zinc-coated steel sheets. Such different defect types have required their respective treatments different from each other, which has resulted in the need for accurate classification of the defect types. The classification of defect types was generally made on the basis of worker's visual inspection; however, it has been increasingly automated in recent years with increase in production-line speed and in surface-appearance requested by users in a rigid manner.

The surface defect inspecting techniques for hot-dip zinc-coated steel sheets are disclosed in Patent Documents 1, 2. Patent Document 1 discloses a dross defect inspecting device configured to classify the surface defects on hot-dip zinc-coated steel sheets as dross and other defects on an upstream side of a skin pass mill. The device is configured to illuminate a surface of a hot-dip zinc-coated steel sheet with light at an angle of 50-80° with respect to a normal line of the steel sheet, and image diffuse reflection light in a direction at an angle of 0-40° with respect to the normal line so as to acquire image signals. Out of the acquired signals, the device is further configured to classify a portion having brightness level lower than a predetermined threshold and area falling within a predetermined range as dross, and classify a portion having brightness level lower than a predetermined threshold and area falling outside a predetermined range as other surface defects. Patent Document 1 discloses the classification of extracted surface defects as: "no harm"; "dross"; "dirt, linear flaw"; "scab, scale"; "hole"; "patterned flaw" based upon determination logic shown in FIG. 5 in Patent Document 1 through the use of three feature quantities: area of surface defects; image brightness of surface defects; aspect ratio of surface defects.

Patent Document 2 discloses a quality control device arranged in a stage prior to a stage in which hot-dip zinc-coated steel sheets are rolled up to obtain coils. The quality control device is configured to, initially, illuminate a surface of a hot-dip zinc-coated steel sheet with light, and image specular reflection light as a reflected light of an illuminated light so as to acquire reflection image signals and perform extraction of image signals indicative of possible defects from acquired reflection image signals, and also image diffuse reflection light as a reflected light of the illuminated light so as to acquire reflection image signals and perform extraction of image signals indicative of possible defects from acquired reflection image signals. The extraction of the image signals indicative of possible defects is performed individually, for the specular reflection light and the diffuse reflection light, through the use of thresholds each set at a certain level of quality. The quality control device is configured to, subsequently, read basic information such as "linear flaw," "non-coating" set in advance, for each defect type, so as to select the image signals of true defects out of the image signals indicative of possible defects and acquire information about distribution of the image signals of true defects for each defect type. The quality control device is configured to, still subsequently, calculate a defect length, for each defect type, based upon acquired information, and determine, on the basis of a ratio of a calculated defect length relative to an entire length of the steel sheet and the like, whether a level of quality is achieved or not.

PRIOR ART DOCUMENTS

Patent Documents

Patent Document 1 Japanese Patent No. 5594071
Patent Document 2 Japanese Unexamined Patent Application Publication No. 2004-151006

Problem to be Solved

The dross defect inspecting device disclosed in Patent Document 1 is configured to determine that, out of image signals of surface defects acquired from diffuse reflection light, a portion having area, in which brightness level is lower than a predetermined threshold, falling within a predetermined range is classified as dross. Surface defects, however, inevitably vary in area, and therefore, there are probabilities that, by the method in Patent Document 1, surface defects (e.g. non-coating, scab, dirt, and the like) showing image with brightness lower in level than that of dross, would erroneously be classified as dross. Further, the device described in claim 2 in Patent Document 1 is configured to determine whether surface defects are classified as dross or other surface defects in consideration of their aspect ratios (forms) as well. Surface defects, however, inevitably vary in aspect ratio, and therefore, there are also probabilities that surface defects such as non-coating, scab, dirt would erroneously be classified as dross.

As described above, it is disclosed in Patent Document 2 that, from image signals obtained by imaging specular reflection light and diffuse reflection light, respectively, image signals indicative of possible defects are extracted through the use of thresholds set individually in advance for the specular reflection light and the diffuse reflection light, and that the image signals of true defects are selected out of the image signals indicative of possible defects by referring to basic information set in advance for each defect type such as "linear flaw," "non-coating." It is not disclosed at all in Patent Document 2 as to any methods for classifying the image signals of possible defects as different defect types (e.g. "linear flaw," "non-coating"). In other words, Patent Document 2 does not disclose any techniques for determining exactly defect types by classifying the surface defects on steel sheets.

SUMMARY OF THE INVENTION

In view of the above-described problems, there is provided the present invention whose objective is to provide a surface defect inspecting device and method for hot-dip coated steel sheets More specifically, the present invention is provided as a surface defect inspecting device and method for hot-dip coated steel sheets that allow high-precision determination by classification of surface defects while relying as little as possible upon the areas, forms, other features of surface defects likely to vary.

Means for Solving Problems

A surface defect inspecting device for hot-dip coated steel sheets, according to the present invention, comprises: an illuminating unit configured to illuminate an imaging target portion on a surface of a hot-dip coated steel sheet; a specular reflection light imaging unit configured to image specular reflection light reflected from the imaging target portion; a diffuse reflection light imaging unit configured to image diffuse reflection light reflected from the imaging target portion; and an image signal processing unit configured to process a specular reflection image signal acquired by the specular reflection light imaging unit as a result of performing imaging and a diffuse reflection image signal acquired by the diffuse reflection light imaging unit as a result of performing imaging. The specular reflection light imaging unit and the diffuse reflection light imaging unit are further configured to simultaneously image light reflected from the imaging target region, and the image signal processing unit is further configured to extract a portion having brightness level lower than a predetermined threshold, as a surface defect portion, from the specular reflection image signal acquired by the specular reflection light imaging unit as a result of performing imaging, and threshold process the diffuse reflection image signal acquired by the diffuse reflection light imaging unit as a result of performing imaging, with respect to a portion corresponding to an extracted surface defect portion, so as to determine a defect type by classifying the extracted surface defect portion.

It is preferable that the image signal processing unit calculates a shift average value of the diffuse reflection image signal acquired by the diffuse reflection light imaging unit as a result of performing imaging of a base texture, and applies a calculated shift average value, as a threshold for threshold processing, to determining a defect type by classifying a portion having brightness level higher than the threshold and a portion having brightness level lower than the threshold, respectively, as different defect types of surface defect from each other.

According to the above-configured surface defect inspecting device for hot-dip coated steel sheets, the simultaneous and combined use of information about brightness of the specular reflection image signals obtained from the specular reflection light and information about brightness of the diffuse reflection image signals obtained from the diffuse reflection light enables high-precision determination by classification of types of surface defects without relying upon the areas, forms, other features of surface defects likely to vary.

A surface defect inspecting method for hot-dip coated steel sheets, according to the present invention, comprises the steps of: illuminating a surface of a hot-dip coated steel sheet; imaging specular reflection light and diffuse reflection light reflected from an imaging target portion on the hot-dip coated steel sheet, respectively; and processing a specular reflection image signal and a diffuse reflection image signal acquired as a result of performing imaging, respectively. In a step of said imaging, the specular reflection light and the diffuse reflection light reflected from the imaging target portion are simultaneously imaged. In a step of said processing, a portion having brightness level lower than a predetermined threshold is extracted, as a surface defect portion, from the specular reflection image signal acquired as a result of performing imaging, and the diffuse reflection image signal acquired as a result of performing imaging is threshold processed, with respect to a portion corresponding to an extracted surface defect portion, so that a defect type is determined by classifying the extracted surface defect portion.

It is preferable that, in a step of said processing, a shift average value of the diffuse reflection image signal acquired as a result of performing imaging of a base texture is calculated, and a calculated shift average value is applied, as a threshold for threshold processing, to determining a defect type by classifying a portion having brightness level higher than the threshold and a portion having brightness level lower than the threshold, respectively, as different defect types of surface defect from each other.

According to the above-configured surface defect inspecting method for hot-dip coated steel sheets, the simultaneous and combined use of information about brightness of the specular reflection image signals obtained from the specular reflection light and information about brightness of the diffuse reflection image signals obtained from the diffuse reflection light enables high-precision determination by classification of types of surface defects without relying upon the areas, forms, other features of surface defects likely to vary.

Advantageous Effects of the Invention

According to the present invention, high-precision determination by classification of surface defects is allowed while relying as little as possible upon the areas, forms, other features of surface defects likely to vary.

BRIEF DESCRIPTIONS OF THE DRAWINGS

For more thorough understanding of the present invention and advantages thereof, the following descriptions should be read in conjunction with the accompanying drawings in which.

DESCRIPTIONS OF EMBODIMENTS OF THE INVENTION

Hereafter, a surface defect inspecting device and method for hot-dip coated steel sheets as an embodiment of the present invention with reference to the drawings. In an embodiment, hot-dip coated steel sheets are exemplified by hot-dip zinc-coated steel sheets.

Figure 1:
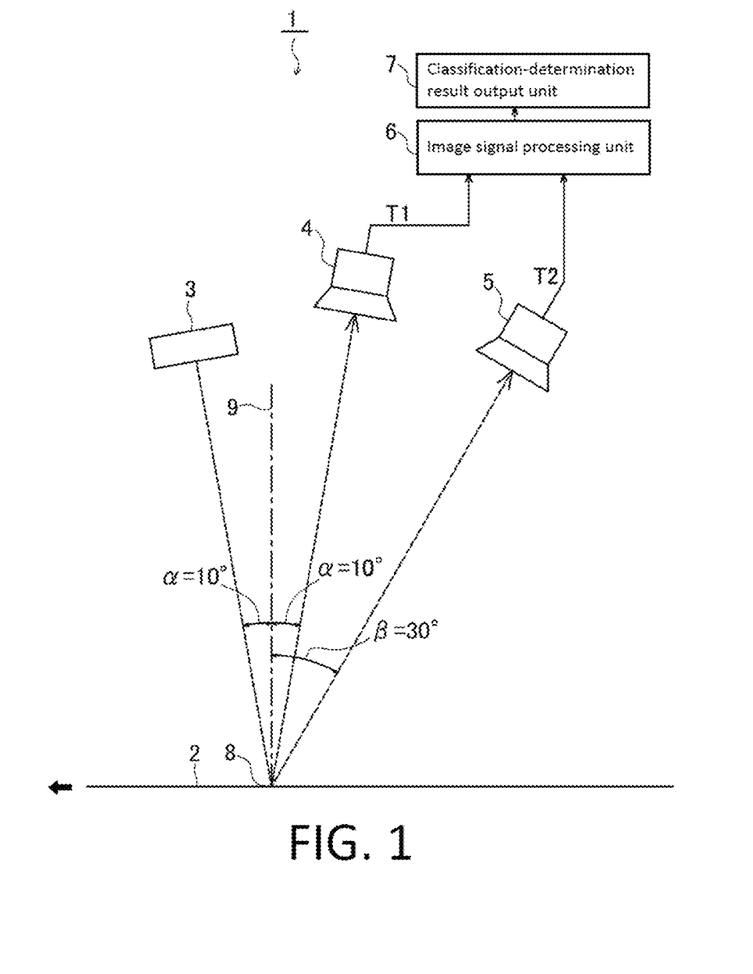
FIG. 1 depicts a structurally exemplified view of a surface defect inspecting device for hot-dip coated steel sheets.

As shown in FIG. 1, a surface defect inspecting device (1) in an embodiment determines defect types by classifying surface defects on a hot-dip zinc-coated steel sheet (2) (hereafter, referred to as "steel sheet (2)") while the steel sheet (2) being conveyed continuously. The device (1) includes an illuminating unit (3), a specular reflection light imaging unit (4), a diffuse reflection light imaging unit (5), an image signal processing unit (6), a classification-determination result output unit (7), and the like.

The illuminating unit (3) illuminates an imaging target portion (8) on a surface of the steel sheet (2). The unit (3) is arranged on a downstream side, along a conveyance direction of the steel sheet (2), with respect to a plane (9) defined virtually as being orthogonal to a conveyance direction of the steel sheet (2) at the imaging target portion (8) (hereafter, occasionally referred to as "orthogonal plane (9)") in such a manner that light is incident on the surface of the steel sheet (2) at a predetermined incidence angle of $\alpha$ ($\alpha$=10° in an embodiment) with respect to the orthogonal plane (9). In an embodiment, as a light source of the illuminating unit (3), an LED line illuminator configured to illuminate the steel sheet (2) in a plate width direction is adopted. The light source of the illuminating unit (3) is not so limitative, however, and halogen, metal halide fluorescent lamps, other than an LED, may be adopted alternatively.

The specular reflection light imaging unit (4) images specular reflection light reflected from the imaging target portion (8) on the surface of the steel sheet (2) illuminated with light by the illuminating unit (3). The specular reflection light imaging unit (4) is, therefore, arranged on an upstream side, along a conveyance direction of the steel sheet (2), with respect to the orthogonal plane (9) in such a manner that the unit (4) receives the specular reflection light at an angle of a with respect to the orthogonal plane (9). In an embodiment, the specular reflection light imaging unit (4) adopts a CCD line sensor camera. It may be replaced by e.g. a CCD area sensor camera. It is to be noted that a spatial resolution for detection by the specular reflection light imaging unit (4) is set appropriately in accordance with defect types of surface defects as detection targets.

The diffuse reflection light imaging unit (5) images diffuse reflection light reflected from the imaging target portion (8) on the surface of the steel sheet (2) illuminated with light by the illuminating unit (3). The diffuse reflection light imaging unit (5) is arranged on an upstream side, along a conveyance direction of the steel sheet (2), with respect to the orthogonal plane (9) in such a manner that the unit (5) receives the diffuse reflection light at an angle of $\beta$ (==30° in an embodiment) with respect to the orthogonal plane (9). In an embodiment, the diffuse reflection light imaging unit (5) also adopts a CCD line sensor camera. It may be replaced by e.g. a CCD area sensor camera. It is to be noted that a spatial resolution for detection by the diffuse reflection light imaging unit (5) is also set appropriately in accordance with defect types of surface defects as detection targets.

The image signal processing unit (6) processes specular reflection signals T1 acquired by the specular reflection light imaging unit (4) as a result of performing imaging and diffuse reflection signals T2 acquired by the diffuse reflection light imaging unit (5) as a result of performing imaging, so as to extract surface defects on the steel sheet (2) and determine defect types by classifying the extracted surface defects. The image signal processing unit (6) includes various arithmetic processors (e.g. a personal computer, PC, installed with a program necessary to carry out classification-determination logic that will be described later). It is to be noted that a result of determination is sent to a host process computer for quality determination.

The classification-determination result output unit (7) transmits by means of displaying or printing, to a present manufacturing process, a subsequent manufacturing process, or users, defect types determined by the image signal processing unit (6) as a result of classifying surface defects. The classification-determination result output unit (7) includes e.g. a monitor, a printer, and the like.

Figure 2:
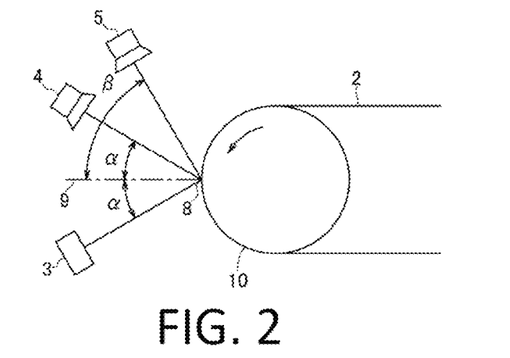
FIG. 2 depicts a status view of a surface defect inspecting device for hot-dip coated steel sheets where the device inspects a surface of a steel sheet when the sheet is conveyed along a roller.

It is to be noted that, as shown in FIG. 1, the surface defect inspecting device (1) inspects a surface of a steel sheet (2) conveyed in a horizontal direction; however, the device (1) can also inspect a surface of a steel sheet (2) being conveyed along an outer peripheral surface of a roller (10) as shown in FIG. 2. Although a place for arranging the surface defect inspecting device (1) is not particularly limitative, it is preferred that the device (1) be arranged in a place where the surface defect inspection is performed in a final process of manufacturing a steel sheet (2). More particularly, it is preferred that the surface defect inspection be performed by the device (1) on a steel sheet (2) at the timing after the temper rolling in a skin pass mill is completed before the winding around a tension reel is commenced.

Figure 3:
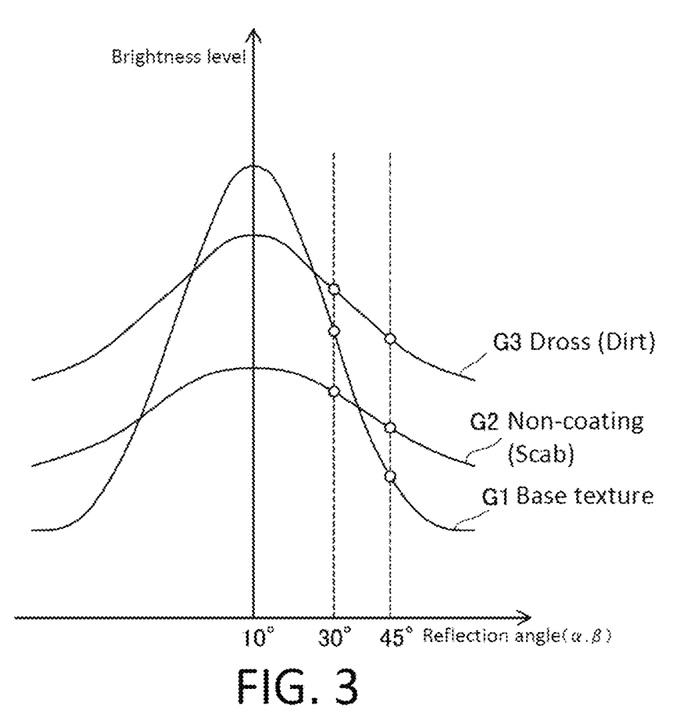
FIG. 3 depicts a graph showing a relation of brightness levels of reflection light as a function of reflection angles with respect to a base texture, non-coating portion, dross portion.

The relation between reflection angles and brightness levels of light reflected from the surface of the steel sheet (2) is qualitatively different for each base texture and defect type of the surface defect. It is preferred that, in view of the above, a light receiving angle $\beta$ of the diffuse reflection light imaging unit (5) be set. The graph shown in FIG. 3 shows the above-described relation in a horizontal axis representing reflection angles and a vertical axis representing brightness levels. The curve G1 shows a relation with respect to reflection from a base texture, the curve G2 shows a relation with respect to reflection from a non-coating or scab portion (hereafter, represented by "non-coating" only), and the curve G3 shows a relation with respect to reflection from a dross or dirt portion (hereafter, represented by "dross" only). The curves G1-G3 all show that each brightness level is the maximum at an angle, which is a specular reflection angle, of 10°, and that, with increase in each reflection angle from a specular reflection angle of 10°, the brightness level decreases. Such decrease in brightness level is much more significant for the base texture in comparison with the non-coating and dross.

In an embodiment, the diffuse reflection light imaging unit (5) is arranged in such a manner that $\beta$ is equal to 30°, that is, in such a manner that a brightness level of reflection light from the dross portion as a reflection surface (curve G3) is higher than a reference level of reflection light from the base texture as a reflection surface (curve G1), and a brightness level of reflection light from the non-coating portion as a reflection surface (curve G2) is lower than the reference level.

Figure 4:
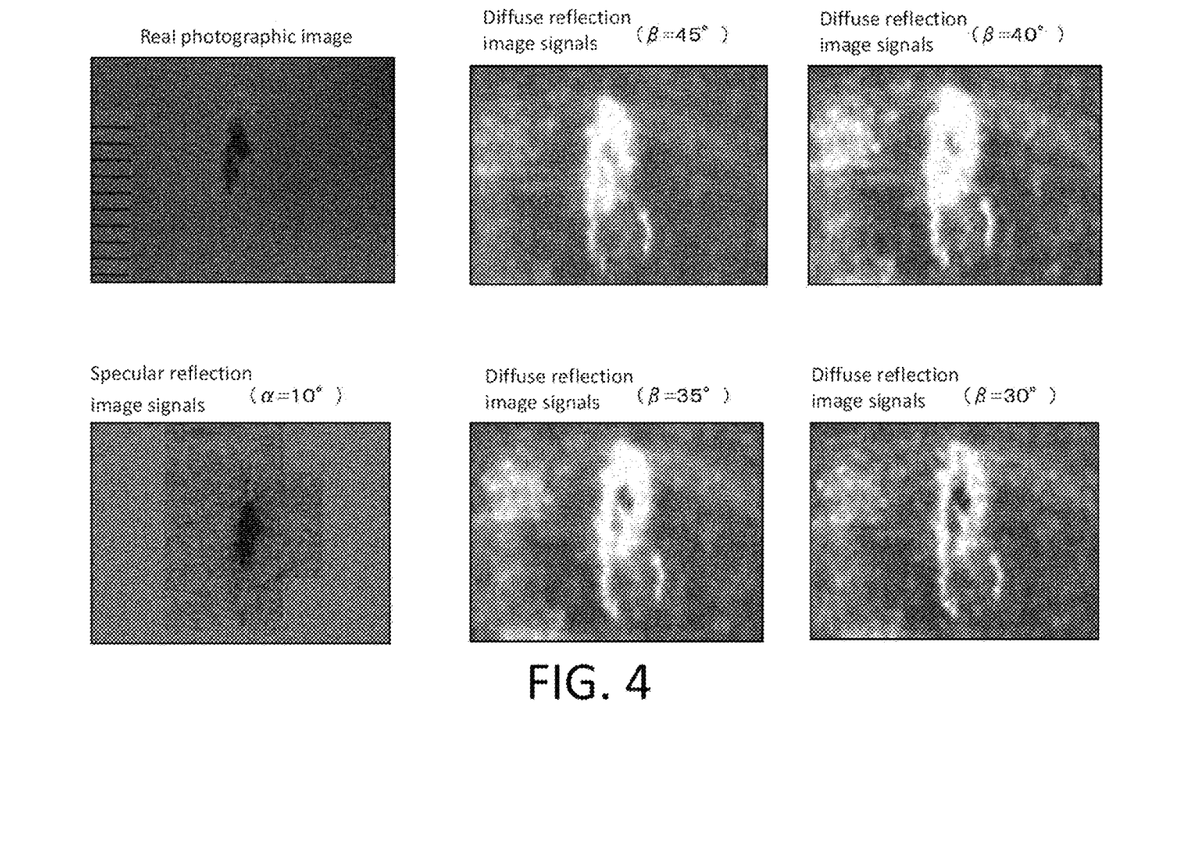
FIG. 4 depicts a variety of pieces of image view of non-coating in dross on a surface of a hot-dip coated steel sheet.

Any pieces of image shown in FIG. 4 are related to non-coating in dross generated on the surface of the steel sheet (2). The non-coating in dross means a surface defect having non-coating inside dross. As shown in FIG. 4, "Real photographic image" represents image taken photographically for the non-coating in dross; "Specular reflection image signals (α=10°)" represent image formed on the basis of specular reflection image signals acquired by the specular reflection light imaging unit (4); and "Diffuse reflection image signals (β=45°)," "Diffuse reflection image signals (β=40°)," "Diffuse reflection image signals (β=35°)," and "Diffuse reflection image signals (β=) 30°)" represent four pieces of image formed on the basis of diffuse reflection image signals acquired by the diffuse reflection light imaging unit (5) tentatively arranged in such a manner that the light receiving angle β is equal to 45°, 40°, 35°, and 30°, respectively.

As shown in "Real photographic image" in FIG. 4, both the non-coating portion and the dross portion out of the non-coating in dross look black (dark) to the naked eye in comparison with the surrounding base texture. Also in "Specular reflection signals (α=10°)," the non-coating and dross portions look black in comparison with the surrounding base texture. On the other hand, in "Diffuse reflection image signals (β=45°)," the non-coating and dross portions look white because a brightness level of diffuse reflection signals is higher for non-coating and dross in comparison with the base texture (see FIG. 3). As β comes closer to a, the non-coating portion gradually blackens, as shown in "Diffuse reflection image signals (β=40°" and "Diffuse reflection image signals (β=35°)." In "Diffuse reflection image signals (β=30°)", the non-coating portion turns black, while the dross portion remains white.

As shown in FIG. 3, the non-coating and dross can be classified for defect-type determination by arranging the diffuse reflection light imaging unit (5) at a reflection angle set in such a manner that a brightness level of light reflected from a dross portion (curve G3) is higher than a reference level, as a threshold, of light reflected from the base texture (curve G1), and a brightness level of light reflected from a non-coating portion (curve G2) is lower than a reference level, as a threshold, of light reflected from the base texture (curve G1). Such approach can be applied not only to classifying for defect-type determination between the non-coating and dross in a limitative manner but also to classifying for defect-type determination among other surface defects.

Figure 5:
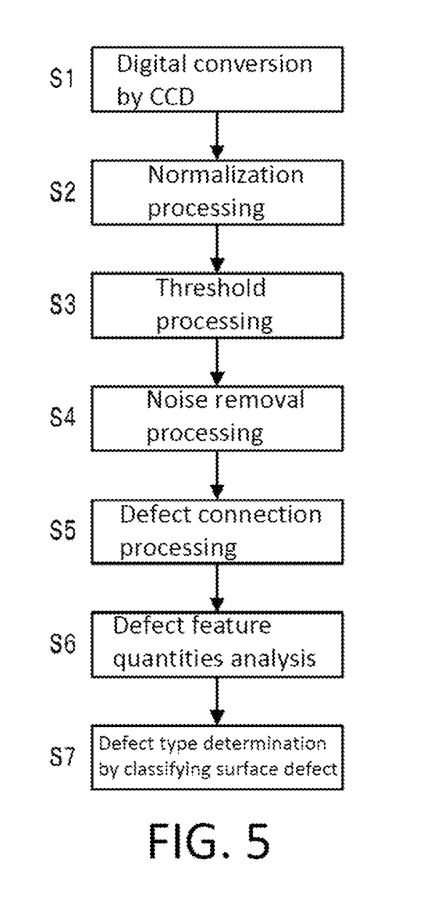
FIG. 5 depicts a flowchart showing steps from detecting defects through image signals acquired by imaging reflection light until determining defect types by classifying detected defects.

Hereafter, steps from detecting defects through image signals acquired by imaging reflection light in the respective reflection light imaging units (4, 5) until determining defect types by classifying detected defects will be explained with reference to FIG. 5.

Initially, the specular reflection light imaging unit (4) and the diffuse reflection light imaging unit (5) image the lights reflected from the surface of the steel sheet (2) and perform digital conversion through the use of CCD to acquire 256-gradation specular reflection image signals T1 and diffuse reflection image signals T2 (S1), respectively (S1).

Figure 7:
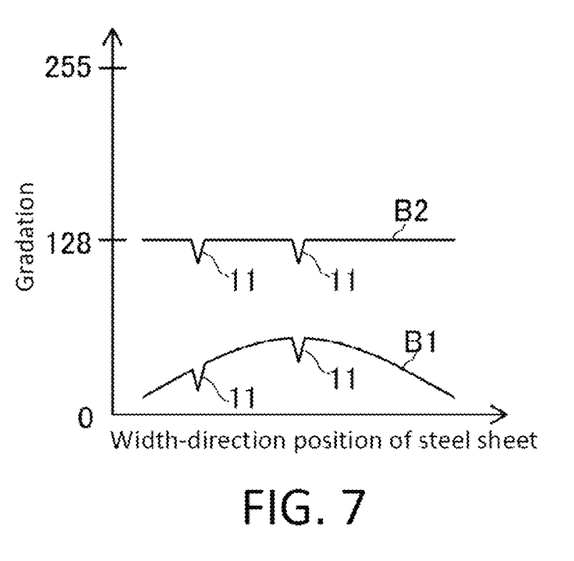
FIG. 7 depicts an explanatory view of normalization processing.

Subsequently, the image signal processing unit (6) performs normalization processing of the specular reflection image signals T1 and the diffuse reflection image signals T2 (S2), and thereafter performs threshold processing (S3) of them. The normalization processing is performed to correct variation and bias in the values of the image signals T1 and T2 mainly due to aberration of the lenses of the reflection light imaging units (4, 5) as well as different illumination conditions in different imaging positions on the steel sheet (2). As the above-described normalization processing, the normal distribution e.g. N (μ, σ²) with respect to the image signals T1 and T2 obtained in S1 is converted to the standard normal distribution N (0, 1²), where mean μ is equal to 0 and standard deviation a is equal to 1, and the mean is further adjusted from 0 to 128 in an offset manner. For instance, as shown in FIG. 7, when the values of the image signals T1 and T2 make a waveform centered along a curve B1 in a shape of gradual increase toward a center from both sides in a width direction of the steel sheet (2) before the normalization processing is performed, the values of the image signals T1 and T2 make a waveform centered along a line B2 without variation with a mean of 128 after the normalization processing is completed. It is to be noted that, as shown in FIG. 7, the vertical axis represents gradation from 0 to 255 and the horizontal axis represents positions in a width direction of the steel sheet (2), and the ends of the curve B1 and the line B2 correspond to the ends of the steel sheet (2), and the projections (11) protruding downward from the curve B1 and the line B2 indicate image signals indicative of defects.

In the threshold processing of the specular reflection image signals T1, the specular reflection image signals T1L having brightness level lower than a predetermined threshold P1 are regarded (extracted) as defect portions. The above-described threshold P1 may be a predetermined constant, while, in an embodiment, the threshold P1 is set to be a value lower than a shift average value of the specular reflection image signals T1 in the imaging range of the specular reflection light imaging unit (4) by a predetermined value.

In the threshold processing of the diffuse reflection image signals T2, for the above-described defect portions (portions on the steel sheet (2) with the specular reflection image signals T1 having brightness level lower than the predetermined threshold P1), the diffuse reflection image signals T2H having brightness level higher than a predetermined threshold P2 are classified as a first defect type (dross or dirt in an embodiment), and the diffuse reflection image signals T2L having brightness level lower than the predetermined threshold P2 are classified as a second defect type (non-coating or scab in an embodiment). The above-described threshold P2 may be a predetermined constant, while, in an embodiment, the threshold P2 is set to be a value lower than a shift average value of the diffuse reflection image signals from the base texture acquired by the diffuse reflection light imaging unit (5).

Figure 8:
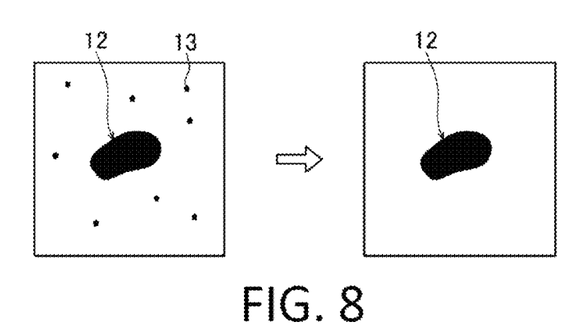
FIG. 8 depicts an explanatory view of noise removal processing.
Figure 9:
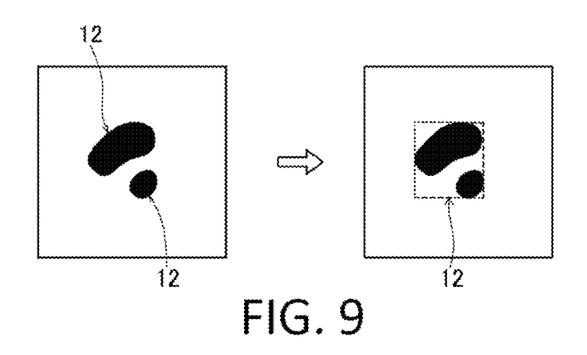
FIG. 9 depicts an explanatory view of defect connection processing.

Still subsequently, the image signal processing unit (6) performs noise removal processing (S4) to extract pixels regarded as being defect portions in the threshold processing of the specular reflection image signals T1, and thereafter performs defect connection processing (S5) of the extracted pixels of defect portions so as to connect thereamong. In the noise removal processing, out of defect pixels (12, 13) detected in the above-described threshold processing, defect pixels (13) in the form of isolated points (minute defects) distinguishable from their neighborhood are regarded as being noises as shown in a left-sided view of FIG. 8, and are changed to normal pixels as shown in right-sided view of FIG. 8. A filter for changing the defect pixels (13) to normal pixels (means for noise removal processing) has been well-known as averaging filter, low-pass filter, Gaussian filter, Laplacian filter, and so forth. In the defect connection processing, e.g., defects (12) adjacent to one another, as shown in a left-sided view of FIG. 9, located in one area (exemplified by a square area surrounded by dashed lines in a right-sided view of FIG. 9) are recognized as being a single defect (12).

Based upon a contour of the single defect (12) recognized in the defect connection processing, the image signal processing unit (6) analyzes the feature quantities: aspect ratio; roundness; direction (a longitudinal direction of the defect with respect to a conveyance direction of the steel sheet (2)) of the single defect (12). Further, the image signal processing unit (6) calculates the densities of pixels in the area inside the contour (i.e. their proportions to all pixels existing in the area inside the contour): pixels regarded as defect portions in the threshold processing for the specular reflection image signals T1; pixels regarded as the first type of defect portions in the threshold processing for the diffuse reflection image signals T2; and pixels regarded as the second type of defect portions in the threshold processing for the diffuse reflection image signals T2 (S6).

Figure 6:
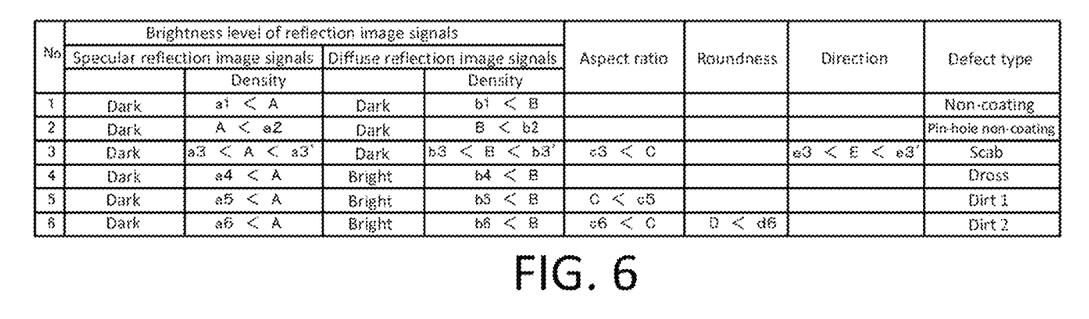
FIG. 6 depicts a table showing threshold conditions on aspect ratio, roundness, direction, density, and the like predetermined for each defect type.

Finally, the image signal processing unit (6) applies threshold conditions on aspect ratio, roundness, direction, and the above-described density predetermined for each defect type, shown in FIG. 6, to the first defect type of defect portions and the second defect type of defect portions so as to further classify the first defect type of defect portion (dross, dirt) into either one of dross, dirt [1] or dirt [2], and the second defect type of defect portions (non-coating, pinhole non-coating, scab) into either one of non-coating, pinhole non-coating, scab (S7). In the threshold conditions in FIG. 6, the capital letters, "A," "B," "C," and "D," represent the actual values obtained in surface defect inspections, and the small letters followed by numbers "a1," "b1," . . . represent predetermined threshold values. Such threshold values are optimal values obtained by repeating experiments and studies on respective defect types of surface defects. "Dark" under "Specular reflection image signals" denotes brightness level lower than the above-described threshold P1. "Dark" under "Diffuse reflection image signals" denotes brightness level lower than the above-described threshold P2, and "bright" under "Diffuse reflection image signals" denotes brightness level higher than the above-described threshold P2.

As clarified from the above descriptions, in the surface defect inspecting device and method for hot-dip coated steel sheets as an embodiment according to the present invention, the simultaneous and combined use of information about brightness of the specular reflection image signals obtained from the specular reflection light and information about brightness of the diffuse reflection image signals obtained from the diffuse reflection light enables high-precision determination by classification of types of defects without relying upon the feature quantities (e.g. aspect ratio, roundness, direction) of surface defects likely to vary. According to an embodiment, at least high-precision determination by classification of defect types as the first defect type and the second defect type without relying upon the above-described feature quantities.

The application of the threshold conditions on the above-described densities makes the high-precision determination by classification in a further detail, and additional application of threshold conditions on the feature quantities such as aspect ratio, roundness, direction makes the high-precision determination by classification in a still further detailed.

In the above-described embodiments, the illuminating angle α of the illuminating unit (3) is 10°, and accordingly, the specular light receiving angle α of the specular reflection light imaging unit (4) is 10°, and the diffuse light receiving angle β of the diffuse reflection light imaging unit (5) is 30°. Such values, however, may also be set to be 10°≤α≤25° and 30°≤β≤45° (on the premise that β fulfills the above-described conditions).

INDUSTRIAL APPLICABILITY

The present invention can be applied to e.g. a surface defect inspecting device and method for hot-dip zinc-coated steel sheets.

REFERENCE NUMERALS

1 Surface defect inspecting device
2 Hot-dip zinc-coated steel sheet (Hot-dip coated steel sheet)
3 Illuminating unit
4 Specular reflection light imaging unit
5 Diffuse reflection light imaging unit
6 Image signal processing unit
8 Imaging target portion
T1 Specular reflection image signals
T2 Diffuse reflection image signals

What is claimed is:

1. A surface defect inspecting device for hot-dip coated steel sheets, comprising:
    an illuminating unit having a light source configured to illuminate an imaging target portion, with light of the light source, on a surface of a hot-dip coated steel sheet;
    a specular reflection light imaging unit having a first light receiver configured to image specular reflection light reflected from the imaging target portion, which is received by the first light receiver;
    a diffuse reflection light imaging unit having a second light receiver configured to image diffuse reflection light reflected from the imaging target portion, which is received by the second light receiver; and
    an image signal processor configured to process a specular reflection image signal acquired by the specular reflection light imaging unit as a result of performing imaging and a diffuse reflection image signal acquired by the diffuse reflection light imaging unit as a result of performing imaging, so that a first defect type and a second defect type, whose diffuse reflection light is lower in brightness level than diffuse reflection light of a base texture when a diffuse reflection angle falls within a predetermined angle-difference range with respect to a specular reflection angle, and is higher in brightness level than diffuse reflection light of a base texture when a diffuse reflection angle falls outside a predetermined angle-difference range with respect to a specular reflection angle, are classified, wherein
    the specular reflection light imaging unit and the diffuse reflection light imaging unit simultaneously image light reflected from the imaging target region, wherein,
    the diffuse reflection angle of the diffuse reflection light imaged by the diffuse reflection light imaging unit is an angle, in accordance with which a brightness level of reflection light from the first defect type as a reflection surface is higher, and a brightness level of reflection light from the second defect type as a reflection surface is lower, in comparison with a reference level defined as a brightness level of reflection light from the base texture as a reflection surface, and wherein
    the image signal processor
    extracts a portion having brightness level lower than a predetermined threshold, as a surface defect portion, from the specular reflection image signal acquired by the specular reflection light imaging unit as a result of performing imaging, and
    threshold processes, through the use of brightness level of reflection light from the base texture as a threshold, the diffuse reflection image signal acquired by the diffuse reflection light imaging unit as a result of performing imaging, with respect to a portion corresponding to an extracted surface defect portion, so as to determine a defect type, by classifying the extracted surface defect portion, as the first defect type and the second defect type.

2. The surface defect inspecting device for hot-dip coated steel sheets according to claim 1, wherein the image signal processor calculates a shift average value of the diffuse reflection image signal acquired by the diffuse reflection light imaging unit as a result of performing imaging of a base texture, and applies a calculated shift average value, as a threshold for threshold processing, to determining a portion having brightness level higher than the threshold as the first defect type, and a portion having brightness level lower than the threshold as the second defect type.

3. A surface defect inspecting method for hot-dip coated steel sheets, comprising the steps of:

Illuminating, by an illuminating unit having a light source, a surface of a hot-dip coated steel sheet;

imaging specular reflection light and diffuse reflection light reflected from an imaging target portion on the hot-dip coated steel sheet by a specular reflection light imaging unit having a first light receiver and a diffuse reflection light imaging unit having a second light receiver, respectively; and processing, by an image signal processor, a specular reflection image signal and a diffuse reflection image signal acquired as a result of performing imaging, respectively, thereby classifying a first defect type and a second defect type, whose diffuse reflection light is lower in brightness level than diffuse reflection light of a base texture when a diffuse reflection angle falls within a predetermined angle-difference range with respect to a specular reflection angle, and is higher in brightness level than diffuse reflection light of a base texture when a diffuse reflection angle falls outside a predetermined angle-difference range with respect to a specular reflection angle, wherein in a step of said imaging by the specular reflection light imaging unit and the diffuse reflection light imaging unit, the specular reflection light and the diffuse reflection light reflected from the imaging target portion are simultaneously imaged, and wherein, the diffuse reflection angle of an imaged diffuse reflection light, in accordance with which a brightness level of reflection light from the first defect type as a reflection surface is higher, and a brightness level of reflection light from the second defect type as a reflection surface is lower, in comparison with a reference level defined as a brightness level of reflection light from the base texture as a reflection surface, and wherein in a step of said processing by the image signal processor, a portion having brightness level lower than a predetermined threshold is extracted, as a surface defect portion, from the specular reflection image signal acquired as a result of performing imaging, and the diffuse reflection image signal acquired as a result of performing imaging is threshold processed through the use of brightness level of reflection light from the base texture as a threshold, with respect to a portion corresponding to an extracted surface defect portion, so that a defect type is determined, by classifying the extracted surface defect portion, as the first defect type and the second defect type.

4. The surface defect inspecting method for hot-dip coated steel sheets according to claim 3, wherein in a step of said processing by the image signal processor, a shift average value of the diffuse reflection image signal acquired as a result of performing imaging of a base texture is calculated, and a calculated shift average value is applied, as a threshold for threshold processing, to determining a portion having brightness level higher than the threshold as the first defect type, and a portion having brightness level lower than the threshold as the second defect type.

* * * * *